(12) United States Patent
Camus et al.

(10) Patent No.: US 7,539,531 B2
(45) Date of Patent: May 26, 2009

(54) CATHETER DEVICE

(75) Inventors: Estelle Camus, Erlangen (DE); Martin Kleen, Furth (DE); Thomas Redel, Poxdorf (DE)

(73) Assignee: Siemens Aktiengesellschaft, Munich (DE)

( * ) Notice: Subject to any disclaimer, the term of this patent is extended or adjusted under 35 U.S.C. 154(b) by 520 days.

(21) Appl. No.: 11/357,539

(22) Filed: Feb. 17, 2006

(65) Prior Publication Data
US 2006/0189928 A1    Aug. 24, 2006

(30) Foreign Application Priority Data
Feb. 18, 2005    (DE) .................. 10 2005 007 574

(51) Int. Cl.
*A61B 6/00* (2006.01)
(52) U.S. Cl. .................. 600/476; 600/478; 600/470
(58) Field of Classification Search .............. 600/470, 600/476, 466, 478, 467
See application file for complete search history.

(56) References Cited

U.S. PATENT DOCUMENTS 6,134,003 A * 10/2000 Tearney et al. .............. 356/479
2003/0230313 A1 * 12/2003 Alipour et al. .............. 128/898
2004/0236414 A1 * 11/2004 Brar et al. .................. 623/1.42
2005/0080313 A1 *  4/2005 Stewart et al. .............. 600/3

FOREIGN PATENT DOCUMENTS

DE              36 20 123 A1    12/1987
WO      WO 2004/012589 A2      2/2004

* cited by examiner

*Primary Examiner*—Long V Le
*Assistant Examiner*—Katherine L Fernandez

(57) ABSTRACT

Catheter device for insertion into a vessel of a human or animal body, comprising a guide catheter and, incorporated in same, an OCT catheter with an OCT imaging device, the guide catheter having a balloon inflatable via a supply line for occluding the vessel, as well as a device for delivering a liquid or gas to the vascular region to be recorded by means of the OCT imaging device, in particular the vascular region located distally to the balloon, wherein there is provided on the guide catheter a second inflatable balloon spaced apart from the first balloon for occluding the vessel, wherein the section of the guide catheter between the two balloons is transparent, at least in sections, to the OCT radiation emittable by the OCT imaging device disposed inside the guide catheter.

9 Claims, 4 Drawing Sheets

CATHETER DEVICE

CROSS REFERENCE TO RELATED APPLICATION

This application claims priority of the German application No. 10 2005 007 574.6 DE filed Feb. 18, 2005, which is incorporated by reference herein in its entirety.

FIELD OF THE INVENTION

The invention relates to a catheter device for insertion into a vessel of a human or animal body, comprising a guide catheter and, incorporated in same, an OCT catheter with an OCT imaging device, the guide catheter having a balloon inflatable via a supply line for occluding the vessel, as well as a device for delivering a liquid or gas to the vascular region to be recorded by means of the OCT imaging device, in particular the vascular region located distally to the balloon.

BACKGROUND OF THE INVENTION

Optical coherence tomography (OCT) is a light-optical imaging method used in the medical field for, among the things, recording images inside a vessel. For this purpose there is provided an OCT catheter with an OCT imaging device which has at least one light guide via which light to be emitted by the OCT imaging device is supplied and light reflected by the vessel wall or the like and recorded by the OCT imaging device is guided to an image processing device disposed extracorporeally. An OCT catheter of this kind is usually incorporated in a guide catheter in which it is displaceable. The two catheters together constitute a catheter device.

In its application in the vascular system, optical coherence tomography is constrained by the fact that transmitted light, typically light in the near infrared region with a wavelength of e.g. 1300 nm, is scattered by blood constituents. Compared to scattering, absorption phenomena at the typical OCT wavelengths are minimal, i.e. scattering effects constitute the primary quality-influencing factor. These scattering effects mean that, during intravascular OCT imaging, the blood must be removed in a suitable manner from the vascular region under examination in order to image the vessel wall. When using a catheter device of the above-mentioned type, this is done by occluding the vessel and therefore the blood flow via a reversibly inflatable balloon disposed on the guide catheter, the occlusion being located preferably proximally to, i.e. upstream of, the imaging location so that only a small amount of liquid or gas for flushing out the residual blood still present in the vessel needs to be introduced distally, i.e. downstream. In this way, once any further inflow is prevented as a result of the occlusion, the vessel can be kept cell-free and good image quality achieved.

However, the problem is that, because of the occlusion of the vessel and therefore of the blood flow, the pressure in the occluded vascular region falls to venous values. This means that, in the case of a normal arterial pressure of approximately 100 mmHg, a pressure of approximately 20 to 30 mmHg obtains in the occluded vascular area. Because of the low-pressure, the anatomy of the vessel, which is expandable like an elastic tube, changes, i.e. the vessel that was dilated at normal arterial pressure contracts as a result of the pressure loss. The OCT images obtained therefore reflect a situation not occurring in natura, i.e. during natural blood flow through the vessel. Also, because of the contracting of the vessel, possible pathologies are sometimes not visible, as they may disappear in vascular folds.

SUMMARY OF THE INVENTION

The object of the invention is therefore to specify a catheter device allowing OCT imaging from an occluded vascular region essentially possessing its natural shape.

To achieve this object for a catheter device of the above-mentioned type, there is provided according to the invention, on the guide catheter, a second inflatable balloon spaced apart from the first balloon for occluding the vessel, the section of the guide catheter between the two balloons being transparent at least in sections to the OCT radiation emittable by the OCT imaging device disposed inside the guide catheter.

The catheter device according to the invention uses two balloons spaced apart from one another which enclose an occluded vascular region between them. The guide catheter is transparent to the OCT radiation at least in sections in the region between the two balloons. To take images, the OCT catheter is inserted until the OCT imaging device is positioned in the appropriate radiation-transparent section, which can be monitored via suitable markings detectable e.g. as part of a partial fluoroscopy and on the basis of which the position of the guide catheter and of the OCT catheter can be detected. Via the known device for delivering a liquid or a gas to the vascular region to be recorded, said vascular region can now be appropriately flushed out and in some cases blood thinning or the like can be performed so that conditions are provided that allow efficient imaging at least in the vascular area occluded for that purpose.

The pressure at which the flushing liquid or gas are supplied or which is set thereby in the occluded vascular region is designed such that as it essentially corresponds to the arterial pressure obtaining in the vessel without occlusion. This means that pressure conditions can be created which at least approximately correspond to the natural values while at the same time allowing complete occlusion of the vascular area to be recorded and creating optimum imaging conditions.

The resulting OCT images consequently show the radial extent or shape of the vessel in as it would appear in natura. Informative images can therefore be obtained which show the real anatomy of the vessel.

Although it is sufficient to make the guide catheter running between the balloons radiation-transparent only in sections, it is advisable for the entire section to be radiation-transparent in order to be able to record corresponding images at any position over a certain length.

The two balloons can be inflatable via a common supply line; in this embodiment they would therefore be simultaneously inflatable. It is also conceivable for each balloon to be inflatable via a separate supply line.

For supplying the flushing liquid or flushing gas, e.g. $CO_2$, there is advantageously provided on the guide catheter, specifically in the section between the balloons, a supply hole via which the liquid or gas fed via the guide catheter, which has a corresponding lumen, can be supplied to the region between the balloons. To set the catheter device, the proximally viewed back balloon can, for example, be inflated first, whereupon flushing liquid or flushing gas is washed into the distal vascular region via the supply hole. When a sufficient quantity has been delivered, e.g. between 0.1 and 30 ml, the second, distal balloon is inflated. In the occluded vascular region there is then exclusively flushing liquid or flushing gas, whereupon imaging can commence.

In order to enable both balloons to be inflated simultaneously, and consequently therefore to occlude the entire vascular section in a single step, there is preferably additionally provided on the guide catheter, specifically in said section, a drain hole for draining supplied liquid or gas from the region between the balloons. In this embodiment, to set the catheter device after positioning of same, the inflation of both balloons, and consequently therefore the occlusion, would take place first, whereupon the flushing liquid or flushing gas is added via the guide catheter and the region between the balloons is flushed out. The residual blood present is flushed via the drain hole into the guide catheter and returned by the latter to the vessel downstream of the distal balloon. When a sufficient flushing amount has been supplied, it is once again ensured that, in the vascular section to be imaged, only flushing liquid or flushing gas, or a sufficient quantity thereof, is present so that optimum imaging can take place. The drain hole is preferably reversibly sealable in order to obviate the need to continuously resupply flushing liquid and to prevent blood from flowing back from the distal vascular region. To seal the drain hole, a sealing element, such as balloon or similar, can be provided which can be inflated, for example, via a supply line. Alternatively there can be provided a sealing flap acting as a one-way valve which moves automatically when subjected to pressure. This means that liquid flowing out of the occluded vascular section causes the valve to open, while any backflow of blood from the distal vascular region is effectively blocked.

A particularly advantageous embodiment of the invention provides for using at least one pressure sensor for detecting the vascular pressure outside the vascular region occluded between the two balloons, thereby enabling the blood pressure in the proximal vascular section preceding the occluded vascular region to be intermittently or continuously measured. The liquid or gas supply can then be controlled according to the measured pressure value. This supply is adjusted e.g. to a time-averaged pressure value. For example, if the usual pressure is approximately 100 mmHg, the pressure can be controlled to this average value. Continuous pressure sensing allows the actual vascular pressure to be monitored, so that any variations in the actual blood pressure which may arise e.g. during treatment depending on the state of health of the patient can be detected immediately, enabling the supply pressure to be re-adjusted accordingly. This applies in respect of both a pressure increase and a pressure reduction. A procedure of this kind is advantageous both where the occluded region is open to the distal vessel, consequently flushing liquid or flushing gas is therefore continuously fed in during imaging, and where the vascular region is closed to the distal vessel after flushing, consequently the flushing liquid or flushing gas is therefore sealed in.

An alternative for measuring the actual pressure outside the vascular region provides for using at least one pressure sensor for detecting the vascular pressure inside the vascular region occluded between the two balloons. The idea underlying this embodiment of the invention is that usually a particular arterial pressure obtains in the vessel, e.g. the approximately 100 mmHg described. With continuous measurement of the actual pressure in the occluded vascular region, the internal vascular pressure can now be adjusted there such that it is constantly e.g. the 100 mmHg mentioned.

A particularly advantageous further development allowing genuine closed-loop pressure control provides for using a control device via which the pressure in the occluded vascular region is adjustable as a function of the pressure obtaining outside the vascular region. The inventive embodiment requires positioning a pressure sensor for detecting the pressure outside the occluded vascular region and a pressure sensor for detecting the pressure inside the occluded vascular region. The two measured values are fed to an appropriate closed-loop control device which controls the supply device for the flushing liquid or flushing gas according to a possible deviation between the actual pressure in the region outside the occluded region, which constitutes the setpoint value, and the actual pressure in the occluded vascular region, which constitutes the actual value. This control device comprises a suitable measurement and control section to which the pressure values are fed as well as a liquid or gas pump or the like. Once again it is of course possible to set the control more or less coarsely or finely. Fine control involves, for example, continuously feeding back the actual pressure in the occluded vascular region in respect of any change in the external pressure; coarse control involves e.g. only average-value control, said average value e.g. only changing if the external pressure outside the occluded vascular region changes by a particular amount.

It is particularly advantageous if the pressure in the occluded region can be controlled via the closed-loop control device as a function of the dynamic variations in the pressure outside the vascular area. This means that fine control takes place in such a way that the actual pressure in the occluded vascular region is tracked directly. The pressure outside the occluded vascular region varies continuously on the basis of heart action depending on the heart phase. In this embodiment of the invention, the systolic and diastolic pressures can therefore be exactly reproduced in the occluded vascular region. Because of this pressure variation, the vessel's anatomy also changes in natura, i.e. the vessel expands somewhat with high pressure and contracts again somewhat as the pressure falls. If precise pressure control is now implemented, the real elastic behavior can be simulated in the occluded region and the behavior of the vascular section during systolic and diastolic pressure variations can be observed via the OCT images as part of an elastography procedure.

BRIEF DESCRIPTION OF THE DRAWINGS

Further advantages, features and details of the invention will emerge from the exemplary embodiments described below and the accompanying drawings in which.

DETAILED DESCRIPTION OF THE INVENTION

Figure 1:
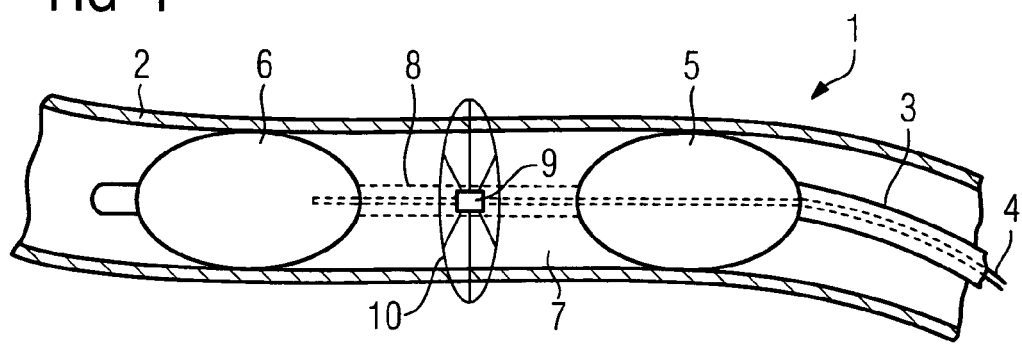
FIG. 1 shows a schematic diagram of a catheter device according to the invention, of which only the region containing the two balloons is illustrated.

FIG. 1 shows the inventive catheter device 1 which, in the example shown, is disposed inside a vessel 2. The catheter device 1 consists of a guide catheter 3, which has a lumen, in which an OCT catheter 4 is disposed in a longitudinally displaceable manner. The specific construction of the guide catheter 3 and the various lumina provided will be explained in greater detail below.

On the guide catheter 3 there is provided a first reversibly inflatable balloon 5, e.g. made of an elastic plastic material, which can be inflated with an inflation gas via a supply line (not shown in greater detail) from a collapsed shape to the inflated shape shown in FIG. 1 in which it bears against the vessel wall, sealing it off. Also shown is a second balloon 6 which is likewise inflatable via a supply line (not shown in further detail), which can be a separate supply line or the same supply line as that leading to the balloon 5, from a collapsed position in which it lies close to the guide catheter to the inflated shape in which it bears against the inner vessel wall as shown in FIG. 1.

Both balloons 5, 6 serve to occlude between them a vascular region 7. The section 8 of the guide catheter 3 located between the balloons which can be spaced several centimeters apart depending on the application is, at least in sections but preferably over its entire length, transparent to the OCT radiation 10 emittable by an OCT imaging device 9 disposed on the OCT catheter 4, so that images can be taken of the inner vascular wall in the occluded vascular section 7.

Figure 2:
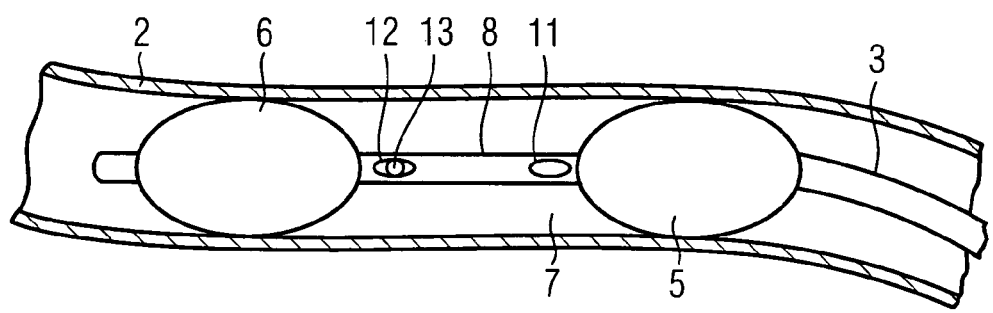
FIG. 2 shows the catheter device from FIG. 1, including the supply and drain holes on the guide catheter.

In order to take images from the occluded vascular region 7 via the OCT imaging device 9, it is necessary to remove the residual blood from this region. For this purpose, FIG. 2 shows a supply hole 11 on the guide catheter 3 or more precisely on the section 8 to which a flushing liquid or flushing gas can be supplied by an external supply device via a lumen or supply line not shown in greater detail in this Fig. but which will be described below.

On the guide catheter 3 or more specifically the section 8 there is additionally provided a drain hole 12 via which flushing liquid or flushing gas supplied to the vascular region 7 via the supply hole 11 can be discharged from said vascular region 7 together with the residual blood present therein. For this purpose a lumen or more specifically a drain line, not shown in greater detail but which will be described below, runs from the drain hole 12 to the vascular region following the balloon 6 where the liquid/blood mixture discharges into the non-occluded vessel.

Assigned to the drain hole 12 is a sealing element 13 which can be inflated by an external device via a supply line not shown in greater detail but which will be described below. This is once again a small balloon with which the drain hole 12 can be tightly sealed. This state is illustrated in FIG. 3 where the sealing element is shown inflated and visibly sealing the drain hole 12.

If OCT images are now to be taken from the inside of the vessel 2, the catheter device 1, which is obviously much longer than the tip section shown in the Figures, is first inserted into the vessel as far as the required location. The two balloons 5, 6, which e.g. have a common supply line, are then preferably inflated by a common external inflation device. The vessel 2 is therefore simultaneously sealed off at two separate locations. At this time, blood is still present in the vascular section 7 enclosed between the balloons 5, 6. This blood must be removed, because otherwise no informative OCT images can be taken because of the continuous scattering by blood corpuscles of the OCT radiation 10 emitted by the OCT imaging device 9. For this purpose, flushing liquid or flushing gas is now pumped along a suitable supply line to the supply hole 11 via a liquid or gas supply device not shown in greater detail in FIGS. 1-3 but which will be described below. The flushing liquid or gas emerging from said supply hole flushes the residual blood present in the vascular region into the drain hole 12 whence it discharges via the drain line (not shown in greater detail) into the vascular region distally following the balloon 6. When a sufficient quantity of liquid or gas has been added, it is ensured that there is no more residual blood present in the vascular region 7, or else in a concentration no longer detrimental to OCT imaging. Once it is ensured that the vascular region 7 has been sufficiently flushed out, the inflatable sealing element 13 is inflated via a suitable supply device not shown in greater detail in FIGS. 1-3 but which will be described below, so that the drain hole 12 is tightly sealed. A saline solution, for example, can be used as the flushing liquid, but it is also possible to use a sugar solution or a dextran solution. Said solutions can also be used to adjust the refractive index of the blood in such a way that any refractive index difference between the blood corpuscles and the liquid is eliminated so that the scattering effect is minimized. $CO_2$, for example, can be used as the flushing gas, as it is very quickly absorbed in the vessel and has no detrimental effects.

A sufficient pressure, which is set e.g. to a predefined value, can now be maintained in the vascular section 7 via the liquid or gas pump. Now that scattering centers are no longer present, OCT imaging can be carried out. Due to the bilateral sealing-off of the vascular region 7 and the possibility of setting a particular pressure within the vascular region 7, a low-pressure occlusion can now be achieved in a particularly advantageous manner without any anatomical change occurring in the occluded vascular region in which the images are being taken.

Figure 3:
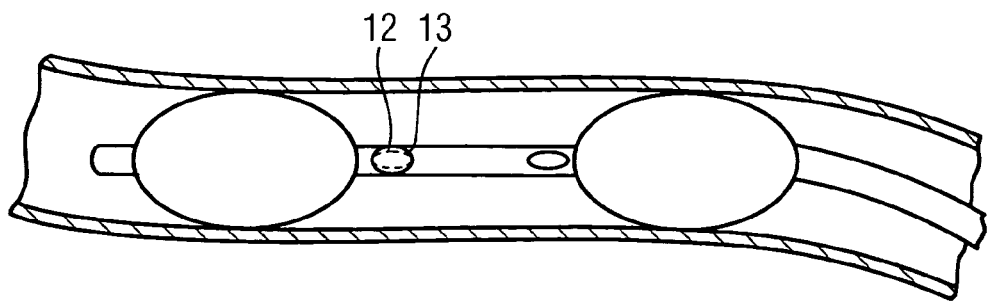
FIG. 3 shows the catheter device from FIG. 2 with the drain hole sealed.
Figure 4:
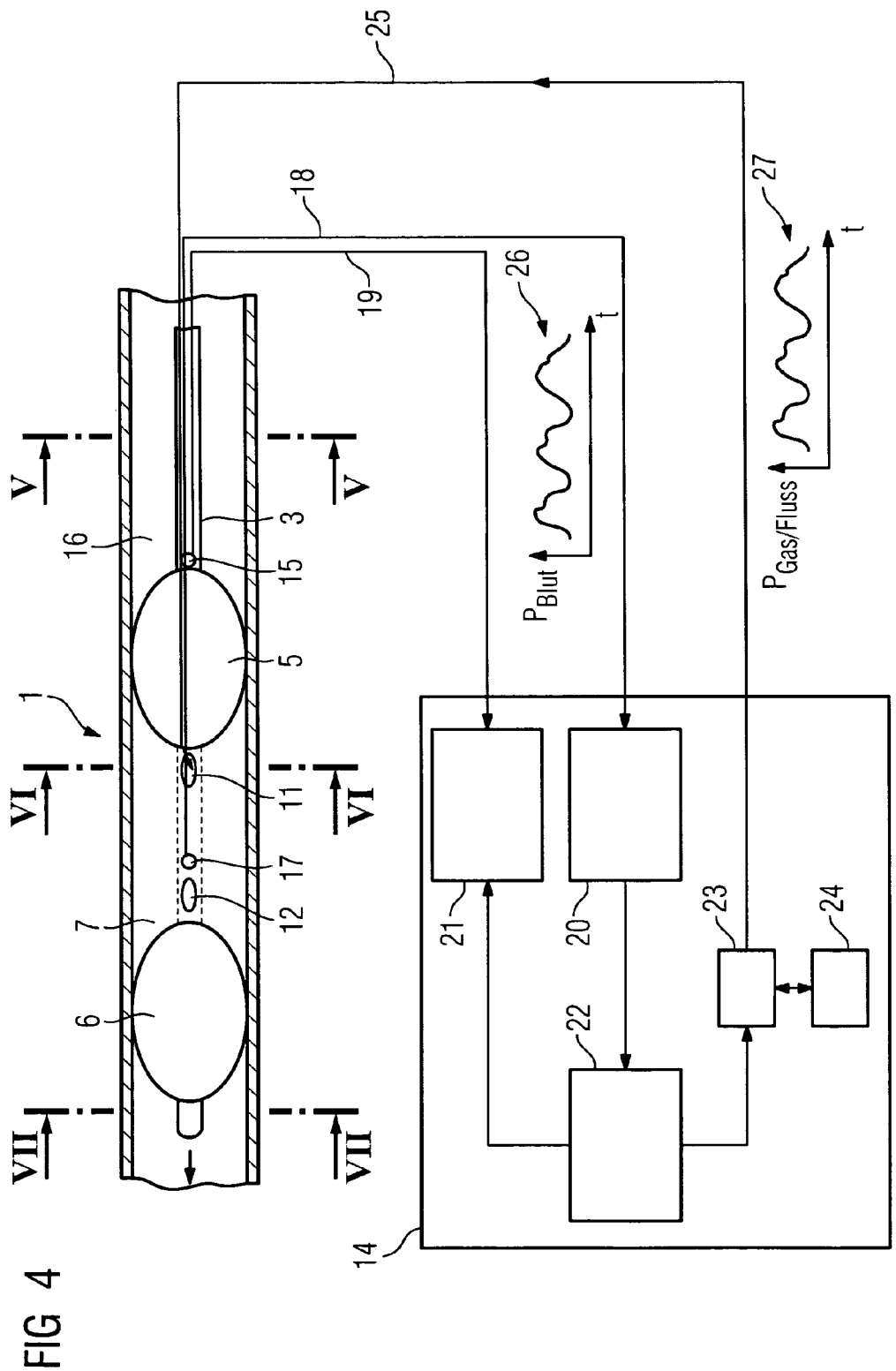
FIG. 4 shows the catheter device according to the invention with two pressure sensors and an associated closed-loop control device.

FIG. 4 shows the catheter device 1 from FIGS. 1 to 3 connected to a control device 14. On the catheter device 1 or more precisely on the guide catheter 3 there are provided two pressure sensors, namely a first pressure sensor 15 which is positioned proximally to the balloon 5 and which measures the pressure in the vascular region 16. This pressure corresponds to the arterial pressure and is, for example, on average approximately 100 mmHg. There is additionally provided a second pressure sensor 17 which measures the pressure in the vascular section 7. The two pressure sensors are connected to the control device 14 via suitable supply lines 18, 19. This device has two recording means 20, 21 which record and possibly store the pressure curves continuously measured by the pressure sensors 15 and 17, the pressure recorded in the vascular section 16 constituting the setpoint, while the pressure recorded in the vascular section 7 constitutes the actual value. The pressure is controlled to the setpoint, for which purpose there is provided a control element 22 which compares the two recorded setpoint and actual values and generates appropriate signals for controlling a pump 23 via which the flushing liquid or flushing gas is pumped from a reserve 24 along the supply line 25 to the supply hole 11.

FIG. 4 shows a time-pressure waveform 26 representing blood pressure, as measured by the pressure sensor 15, versus heart activity. Said blood pressure can be corrected in the vascular section 7 as part of fine control, i.e. the pump 23 is controlled such that the control action is based on a control curve 27 corresponding to the time-pressure curve 26. The pressure conditions in the vascular region 7 are therefore precisely those actually obtaining in the vascular region 16. Dynamic pressure variations can therefore be exactly reproduced, so that the actual vascular movements can also be visually monitored in the occluded region as part of an elastography. In each case it is achieved that the vessel can be imaged in its natural anatomy.

Figure 5:
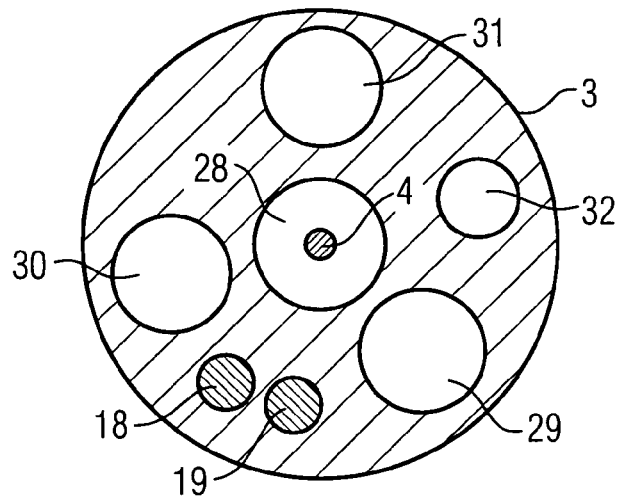
FIGS. 5 to 7 show various sectional views through the guide catheter at the positions V-V, VI-VI and VII-VII in FIG. 4.

FIG. 5 schematically illustrates a sectional view through the guide catheter 3 along the line or plane V-V in FIG. 4, showing a central interior lumen 28 into which the OCT catheter 4 is inserted.

Another lumen 29 leads to the proximal balloon 5. Gas can be fed in/out via said lumen 29 to inflate/deflate the balloon 5.

A third lumen 30 leads to the distal balloon 6 which can be inflated or deflated via said lumen 30. It should be noted at this juncture that separate lumina 29 and 30 are provided for balloons 5 and 6 respectively. It is of course conceivable for both balloons 5, 6 to be served via a single lumen.

A fourth lumen 31 is provided for supplying the flushing liquid or flushing gas. This lumen 31 leads to the supply hole 11.

Additionally provided is the supply line 18 which leads to the pressure sensor 15, and the supply line 19 which leads to the pressure sensor 17.

Finally there is provided a fifth lumen 32 via which the sealing element 13 can be inflated or deflated. The appropriate lumina 29, 30 and 32 are coupled to corresponding gas supply or withdrawal devices in the form of suitable pumps or the like, where possible one pump serving all the lumina and appropriate valve or actuating elements being provided via which the relevant lumina can be opened or closed. The lumen 31 is coupled to the pump 23. The two lines 18, 19 are connected to the control device 14 as described.

Figure 6:
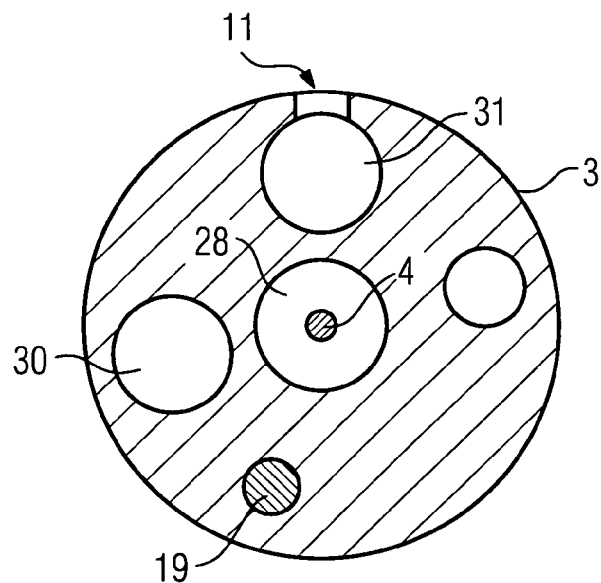

FIG. 6 shows a sectional view along the line or plane VI-VI from FIG. 4. Also shown here is the interior lumen 28 with the OCT catheter 4, the lumen 30 which leads to the distal balloon 6, as well as the lumen 32 leading to the valve element 13. Here the sectional plane shown passes through the supply hole 11 into which the lumen 31 runs and from which the flushing liquid or flushing gas enters the vascular region 7.

Figure 7:
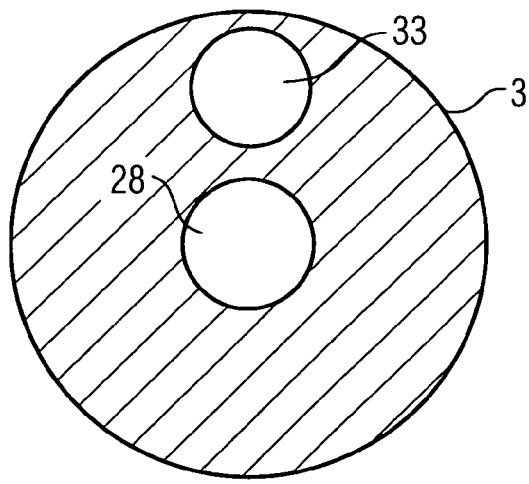

FIG. 7 finally shows a sectional view of the guide catheter 3 along the line or plane VII-VII. This shows the central lumen 28, said lumen no longer being absolutely necessary in this region. Additionally shown is a sixth lumen 33 which is connected to the drain hole 12 and via which the blood flushed out of the vascular region 7 discharges into the downstream vascular region.

Figure 8:
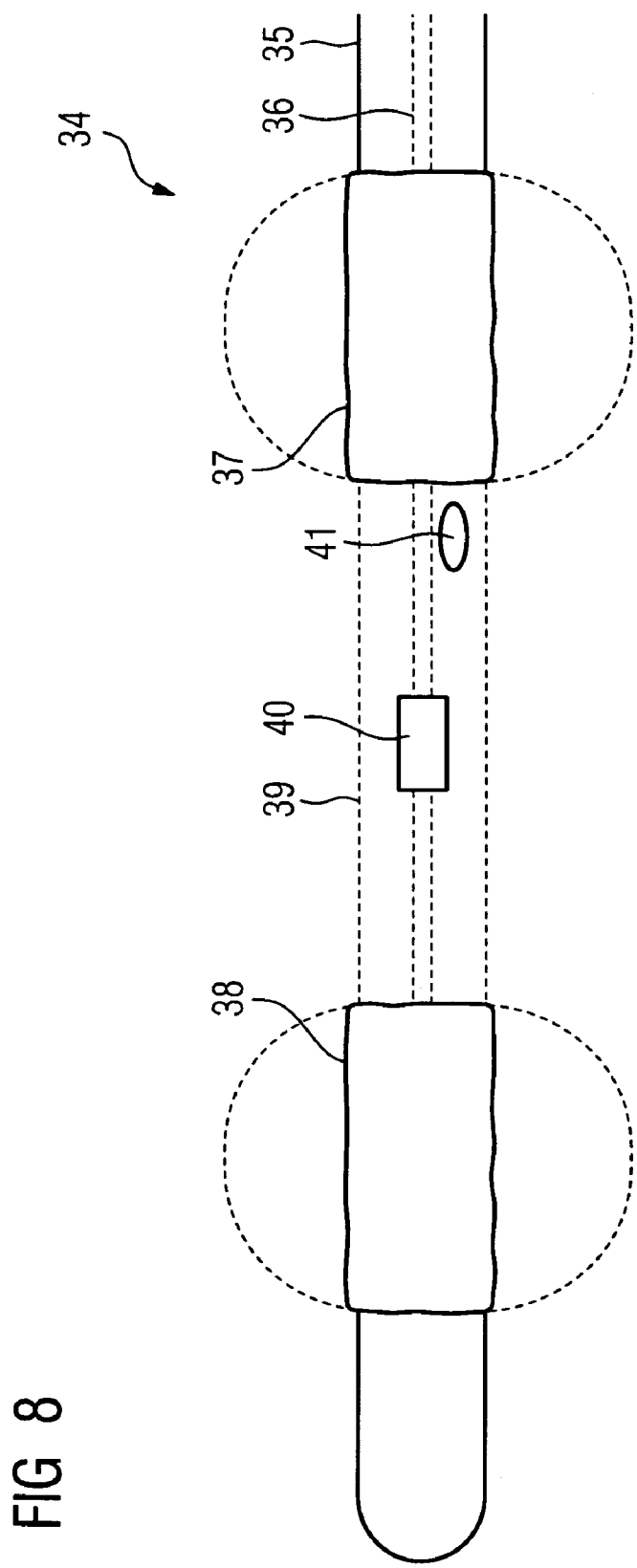
FIG. 8 shows a schematic diagram of the catheter device according to the invention in a second embodiment.

FIG. 8 shows another catheter device 34 according to the invention. This also consists of a guide catheter 35 in which an OCT catheter 36 is displaceably accommodated in a suitable lumen not shown in greater detail. On the guide catheter 35 there are again provided two balloons 37, 38 which are shown in FIG. 8 in the collapsed, i.e. uninflated position. The inflated shapes are represented by the dashed lines. The section 39 of the guide catheter between the two balloons 37, 38 is once again transparent to the OCT radiation emitted by the OCT imaging device 40. In a corresponding manner to that described with reference to FIGS. 5, 6, and 7, there are provided on the guide catheter suitable lumina along which the OCT catheter 36 is guided as described and which are connected to the balloons 37, 38 in order to inflate same. In this embodiment also, each balloon 37, 38 is connected to its own lumen, as described in FIG. 5, i.e. each balloon 37, 38 can be inflated separately. Additionally shown is a supply hole 41 provided on the section 39 via which flushing liquid or flushing gas, which is likewise supplied via a separate lumen, can discharge into the vascular region. The relevant lumina are obviously connected to corresponding devices for supplying gas, for inflating the balloons 37, 38 or for supplying the flushing liquid, even though this is not shown in greater detail here. Reference is made to the embodiments in FIG. 4 in so far as the functions are the same. The OCT catheter, like the OCT catheter 4, is obviously connected to a corresponding OCT image processing unit, even though no such unit is shown in greater detail in FIGS. 1 to 7.

For this catheter device, setting and occluding take place differently from the catheter device 1. The catheter device 34 is first inserted in the vessel, whereupon, on reaching the required position, which can once again be monitored via a suitable fluoroscopy (for which purpose appropriate x-ray markings or the like are provided on the OCT catheter and on the guide catheter), the balloon 37 is inflated first. The vessel is therefore initially occluded at a first proximal location. Flushing liquid or flushing gas is then pumped into the distal vascular region via the supply device 41 by means of a liquid or gas pump. When a sufficient quantity of liquid or gas has been pumped, e.g. 0.1-20 ml, and assuming that a vascular section at least corresponding to the distance between the two balloons 37, 38 has been flushed free of blood, a second balloon 38 is now inflated via a suitable pump. The vessel is therefore occluded at the second location, so that altogether the vascular section between the two balloons 37, 38 is closed on both sides. It is filled with flushing liquid or the like so that optimum OCT imaging can take place.

Although in this embodiment no pressure sensors are provided, such sensors can be provided. Without pressure sensors, for example, a constant pressure of e.g. 100 mmHg is continuously set, i.e. a pressure corresponding to an empirical value for the pressure obtaining in the usually unoccluded vascular region. Genuine closed-loop control, as described with reference to FIG. 4, is not provided in this embodiment. Nevertheless, the heart rhythm can be recorded, for example, via a simultaneously performed ECG, and the pump via which liquid is forced through the supply hole 41 into the occluded vascular region and via which the internal pressure in the vascular region is defined, can be controlled as a function of said heart rhythm. This means that a certain minimum pressure is continuously present which is defined on an average pressure defined via the pump where it is e.g. adjustable and readable. For this embodiment a different mode of setting and of operation is therefore required, as no drain hole and no pressure sensors are provided here.

The catheter device is moved to the location to be examined via a guide wire previously inserted in the vessel and which is accommodated in a pocket (not shown in greater detail here) on the guide catheter. On reaching the required position, the guide wire is withdrawn slightly and moved out of the region to be recorded as an OCT image, for which purpose the pocket must be made long enough to ensure that the guide wire does not slip out accidentally. It does not therefore interfere with the OCT imaging. When imaging is complete, the guide wire can be advanced again in order, if required, to withdraw the balloon catheter from the vessel.

All in all, the catheter devices according to the invention allow low-pressure occlusion with very low inflation pressure of the balloons (unlike the high pressures used for arterial dilatation, and where powerful vasodilation is required), combined with the possibility of imaging the vessel in its actual geometrical relationships as in the unoccluded state, thereby increasing the diagnostic value. The volume of the required flushing liquid or flushing gas administered to the patient is greatly reduced, which diminishes the risk of interrupting the blood supply, as the blood remaining in the capillaries is not flushed out when the blood supply is interrupted.

The invention claimed is:

1. A catheter device for insertion into a vessel of a human or animal body, comprising:
    a guide catheter having a balloon inflatable via a supply line for occluding the vessel and a device for delivering a liquid or gas to a vascular region to be recorded by an OCT imaging device, wherein the vascular region is located distally to the balloon;
    an OCT catheter incorporated within the guide catheter with the OCT imaging device; and
    a second inflatable balloon on the guide catheter spaced apart from the first balloon for occluding the vessel,
    wherein at least a portion of the section of the guide catheter between the two balloons is transparent to an OCT radiation emittable by the OCT imaging device disposed inside the guide catheter and there is provided at least one pressure sensor for measuring the vascular pressure outside the vascular region occluded between the two balloons and there is provided at least one pressure sensor for measuring the vascular pressure inside the vascular region occluded between the two balloons, and there is provided a closed-loop control device via which the pressure in the occluded vascular region is controllable as a function of the pressure obtained outside the vascular regions.

2. The catheter device according to claim 1, wherein the entire section of the guide catheter between the two balloons is radiation-transparent.

3. The catheter device according to claim 1, wherein the two balloons are inflatable via a common supply line.

4. The catheter device according to claim 1, wherein the two balloons are inflatable via a separate supply line.

5. The catheter device according to claim 1, further comprising a supply hole on the guide catheter on the section between the balloons through which the liquid or the gas can be supplied to the region between the balloons.

6. The catheter device according to claim 5, further comprising a drain hole on the guide catheter on the section between the balloons, for draining supplied liquid or gas from the region between the balloons.

7. The catheter device according to claim 6, wherein the drain hole is reversibly sealable.

8. The catheter device according to claim 7, further comprising sealing element to seal the drain hole, the sealing element is inflatable via a supply line or a sealing flap that moves automatically when pressure is applied.

9. The catheter device according to claim 1, wherein the pressure in the occluded region is controllable via the control device as a function of the dynamic variations in the pressure outside the vascular region.

* * * * *